(12) United States Patent
Giocondo, Jr.

(10) Patent No.: US 8,105,371 B1
(45) Date of Patent: Jan. 31, 2012

(54) COMFORT ENHANCING VEST SYSTEM

(76) Inventor: Francis J. Giocondo, Jr., Odessa, FL (US)

(*) Notice: Subject to any disclaimer, the term of this patent is extended or adjusted under 35 U.S.C. 154(b) by 0 days.

(21) Appl. No.: 12/930,583

(22) Filed: Jan. 11, 2011

Related U.S. Application Data (63) Continuation-in-part of application No. 12/080,913, filed on Apr. 7, 2008, now abandoned.

(51) Int. Cl.
*A61F 7/00* (2006.01)
*A41D 1/04* (2006.01)

(52) U.S. Cl. ............. 607/108; 607/112; 607/114; 2/102

(58) Field of Classification Search .................. 607/108, 607/112, 114; 2/102
See application file for complete search history.

(56) References Cited

U.S. PATENT DOCUMENTS

| | | | | |
|---|---|---|---|---|
| 571,543 A * | 11/1896 | Sprague | ............................. | 2/102 |
| 939,871 A * | 11/1909 | Sherman | ............................. | 2/94 |
| 1,520,962 A * | 12/1924 | North | ................................. | 2/102 |
| 2,403,676 A * | 7/1946 | Modlinski | ............................. | 2/94 |
| 2,648,325 A * | 8/1953 | Siple | ............................... | 126/204 |
| 3,809,096 A * | 5/1974 | York | ................................ | 607/108 |
| 3,843,969 A * | 10/1974 | George et al. | ........................ | 2/2.5 |
| 3,950,789 A * | 4/1976 | Konz et al. | ............................ | 2/93 |
| 4,061,897 A * | 12/1977 | Thykeson | ............................. | 219/211 |
| 4,534,354 A * | 8/1985 | Bonner et al. | ................. | 607/108 |
| 4,543,671 A * | 10/1985 | Monk | ................................ | 2/158 |
| 4,580,408 A * | 4/1986 | Stuebner | ........................ | 62/259.3 |
| 4,586,506 A * | 5/1986 | Nangle | ............................ | 607/112 |
| 4,625,729 A * | 12/1986 | Roney | ............................. | 607/108 |
| 4,696,066 A * | 9/1987 | Ball et al. | ............................. | 2/272 |
| 4,886,063 A * | 12/1989 | Crews | ................................ | 607/112 |
| 4,972,832 A * | 11/1990 | Trapini et al. | ................. | 607/108 |
| 5,031,244 A * | 7/1991 | Inagaki | ................................ | 2/102 |
| 5,038,779 A * | 8/1991 | Barry et al. | ..................... | 607/108 |
| 5,063,614 A * | 11/1991 | McSheffery | ........................ | 2/94 |
| 5,072,455 A * | 12/1991 | St. Ours | ............................. | 2/81 |
| 5,146,625 A * | 9/1992 | Steele et al. | ........................ | 2/102 |
| 5,215,080 A * | 6/1993 | Thomas et al. | ................ | 607/112 |
| 5,336,255 A * | 8/1994 | Kanare et al. | ................. | 607/149 |
| 5,393,462 A * | 2/1995 | Avery | ........................... | 516/102 |
| 5,484,448 A * | 1/1996 | Steele et al. | ................. | 607/108 |
| 5,507,794 A * | 4/1996 | Allen | ................................ | 607/112 |
| 5,606,746 A * | 3/1997 | Shelton et al. | .................... | 2/102 |
| 5,692,238 A * | 12/1997 | Watson, Jr. | ....................... | 2/102 |
| 5,826,273 A * | 10/1998 | Eckes | ................................ | 2/69 |
| 5,871,458 A * | 2/1999 | Detty | ................................ | 602/27 |
| 5,928,275 A * | 7/1999 | Yates et al. | ..................... | 607/112 |
| 6,440,159 B1 * | 8/2002 | Edwards et al. | ............. | 607/108 |
| 6,440,160 B1 * | 8/2002 | Cordani et al. | ............... | 607/114 |
| 6,582,383 B2 * | 6/2003 | Horning | ........................... | 602/60 |
| 6,736,834 B1 * | 5/2004 | Kumar et al. | .................... | 607/96 |
| 6,945,988 B1 * | 9/2005 | Jones | ............................. | 607/108 |
| 6,974,470 B2 * | 12/2005 | Tsunakawa et al. | .......... | 607/109 |
| 7,041,124 B2 * | 5/2006 | Purcell | ........................... | 607/112 |
| 7,120,938 B2 * | 10/2006 | Ichigaya | ........................... | 2/272 |
| 2002/0016984 A1 * | 2/2002 | Poholski | ............................. | 2/94 |
| 2004/0186539 A1 * | 9/2004 | Nozik et al. | ................. | 607/108 |
| 2005/0049661 A1 * | 3/2005 | Koffroth | ...................... | 607/108 |

(Continued)

*Primary Examiner* — Roy Gibson
*Assistant Examiner* — Kaitlyn Smith (57) ABSTRACT

A vest has a front, a back, a left side, a right side, and top and bottom edges. A plurality of fixed coupling strips is secured to the vest in pairs. The strips of each pair are vertically oriented and spaced apart. The fixed coupling strips include long front and back pairs and short side pairs. A plurality of similarly configured envelopes is provided. A pair of repositionable coupling strips are secured to each envelope in a horizontal orientation.

1 Claim, 5 Drawing Sheets

U.S. PATENT DOCUMENTS

2006/0036304 A1* 2/2006 Cordani et al. ............... 607/108
2006/0090240 A1* 5/2006 McKenzie et al. ............. 2/102
2006/0247745 A1* 11/2006 Thompson ................... 607/108
2007/0299489 A1* 12/2007 Francis et al. ................ 607/108
2008/0201818 A1* 8/2008 Nilforushan et al. ............... 2/69

* cited by examiner

COMFORT ENHANCING VEST SYSTEM

RELATED APPLICATION

The present patent application is a continuation-in-part of U.S. patent application Ser. No. 12/080,913 filed Apr. 7, 2008, now abandoned the subject matter of which is incorporated herein by reference.

BACKGROUND OF THE INVENTION

1. Field of the Invention

The present invention relates to a comfort enhancing vest system and more particularly pertains to enabling the selective application of warmth to various portions of a wearer's body through repositionable warming envelopes and thermal packets.

2. Description of the Prior Art

The use of garments of known designs and configurations is known in the prior art. More specifically, garments of known designs and configurations previously devised and utilized for the purpose of warming the body of a wearer through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,038,779 issued Aug. 13, 1991 to Barry relates to a Therapeutic Garment. Barry utilizes heat packets in pockets fixedly stitched to the outside of a garment. Barry does not provide for repositionable interior and exterior pockets and packets nor does Barry provide for packets and pockets at various elevations at the front and sides. U.S. Pat. No. 3,950,789 issued Apr. 20, 1976 to Konz relates to a Dry Ice Cooling Jacket. Konz utilizes cooling packets in pockets positionable at predetermined locations on the inside of a garment. Konz does not provide for repositionable interior and exterior pockets and packets nor does Konz provide for packets and pockets at various elevations at the front and back and sides. U.S. Patent Application Publication 2006/0036304 published Feb. 16, 2006 to Cordani relates to a Thermal Garment System and Method of Using the Same. Cordani utilizes cooling packets in pockets positionable at predetermined locations on the sides of a garment. Cordani does not provide for repositionable interior and exterior pockets and packets nor does Cordani provide for packets and pockets at various elevations at the front and back and sides. U.S. Pat. No. 5,605,144 issued Feb. 25, 1997 to Simmons relates to a Heating Garment with Pouch for Accommodating Inserted Heating Packets. Lastly, U.S. Pat. No. 7,022,950 issued Apr. 4, 2006 to Haas relates to a Thermal Warming Device.

Nothing in the prior art allows for providing different temperatures to different parts of the human body elevationally as well as circumferentially. The present invention provides for such different temperatures both elevationally as well as circumferentially. The benefits from such different temperatures are considered evidenced by the Declaration of Expert Witness Under 35 U.S.C. 1.132 submitted in the parent patent application of the present application. The subject matter of such Declaration is incorporated by reference into this patent application.

While these devices fulfill their respective, particular objectives and requirements, the aforementioned patents do not describe a comfort enhancing vest system that allows for enabling the selective application of warmth to various portions of a wearer's body through repositionable warming envelopes and thermal packets.

In this respect, the comfort enhancing vest system according to the present invention substantially departs from the conventional concepts and designs of the prior art, and in doing so provides an apparatus primarily developed for the purpose of enabling the selective application of warmth to various portions of a wearer's body through repositionable warming envelopes and thermal packets.

Therefore, it can be appreciated that there exists a continuing need for a new and improved comfort enhancing vest system which can be used for enabling the selective application of warmth to various portions of a wearer's body through repositionable warming envelopes and thermal packets. In this regard, the present invention substantially fulfills this need.

SUMMARY OF THE INVENTION

In view of the foregoing disadvantages inherent in the known types of garments of known designs and configurations now present in the prior art, the present invention provides an improved comfort enhancing vest system. As such, the general purpose of the present invention, which will be described subsequently in greater detail, is to provide a new and improved comfort enhancing vest system and method which has all the advantages of the prior art and none of the disadvantages.

To attain this, the present invention essentially comprises a comfort enhancing vest system. First provided is a woven cotton vest. The vest has a front. The vest has a back. The vest has a left side. The vest has a right side. The sides are provided between the front and back. The vest also has a top. The top has a neck hole. The top has a bottom edge. The front has a centrally positioned, vertically oriented opening. The front has snaps. In this manner the opening is selectively joined during use. Further in this manner the opening is separated during putting on and taking off of the vest. The vest has a left arm hole. The left arm hole is provided in the left side beneath the top. The vest has a right arm hole. The right arm hole is provided in the right side beneath the top and spaced from the bottom edge.

A plurality of exterior and interior fixed coupling strips is provided next. The fixed coupling strips are secured to the vest in pairs. The strips of each pair are vertically oriented and spaced apart by between 3 inches and 4 inches. The fixed coupling strips include a long left front pair. The fixed coupling strips include a long right front pair. The fixed coupling strips include a long left back pair. The fixed coupling strips also include a right back pair. The long pairs are between 17 inches and 20 inches in length. The fixed coupling strips include a short left side pair. The short left side pair is provided between the left arm hole and the bottom edge. The fixed coupling strips include a short right side pair. The short right side pair is provided between the right arm hole and the bottom edge. The short pairs have a length of between 65 percent and 70 percent of the length of the long pairs. The strips of each pair are spaced from the next adjacent strip by between 3.5 inches and 4.5 inches.

Further provided is a plurality of similarly configured rectangular envelopes, each between 3 inches and 4 inches per side. Each envelope has a front panel. The front panel has a front face. Each envelope has a rear panel. The rear panel has a rear face. The panels are joined peripherally. Each envelope has an open upper edge. The upper edge is horizontally disposed. The upper edge has hook and loop closures. In this manner the upper edge is opened and closed. Each envelope has a plurality of repositionable coupling strips. The repositionable coupling strips are secured to the rear faces of the envelopes in pairs. The repositionable coupling strips of each pair are horizontally oriented and spaced apart by between 3 inches and 4 inches. The repositionable coupling strips include one pair of strips for each envelope.

Provided last is a heat generating thermal packet. The heat generating thermal packet is in a generally rectangular configuration between 2.5 and 3.5 inches on a side. The thermal packet is essentially flat for removable positioning within an envelope. Each thermal packet will generate heat when rubbed or when materials filling the packet are exposed to air. In this manner heat is generated for a predetermined period of time. Further in this manner an adjacent portion of a user's body is warmed. Two vertically spaced envelopes with thermal packets are positionable on each side. Two vertically spaced envelopes are positioned between a side and a front fixed coupling strip. Two vertically spaced envelopes are also positioned between a side and a rear fixed coupling strip. Three vertically spaced envelopes with thermal packets are positionable on each long pair of fixed coupling strips. Three vertically spaced envelopes are positioned between the front left and front right fixed coupling strips. Three vertically spaced envelopes are also positioned between the rear left and rear right fixed coupling strips.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved comfort enhancing vest system which has all of the advantages of the prior art garments of known designs and configurations and none of the disadvantages.

It is another object of the present invention to provide a new and improved comfort enhancing vest system which may be easily and efficiently manufactured and marketed.

It is further object of the present invention to provide a new and improved comfort enhancing vest system which is of durable and reliable constructions.

An even further object of the present invention is to provide a new and improved comfort enhancing vest system which is susceptible of a low cost of manufacture with regard to both materials and labor, and which accordingly is then susceptible of low prices of sale to the consuming public, thereby making such comfort enhancing vest system economically available to the buying public.

Even still another object of the present invention is to provide a comfort enhancing vest system for enabling the selective application of warmth to various portions of a wearer's body through repositionable warming envelopes and thermal packets.

Lastly, it is an object of the present invention to provide a new and improved comfort enhancing vest system. A vest has a front, a back, a left side and a right side. The vest also has a top and a bottom edge. A plurality of fixed coupling strips is secured to the vest in pairs. The strips of each pair are vertically oriented and spaced apart. The fixed coupling strips include long pairs front and back and short side pairs. A plurality of similarly configured envelopes is provided. A pair of repositionable coupling strips are secured to each envelope in a horizontal orientation.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figures 1, 2:
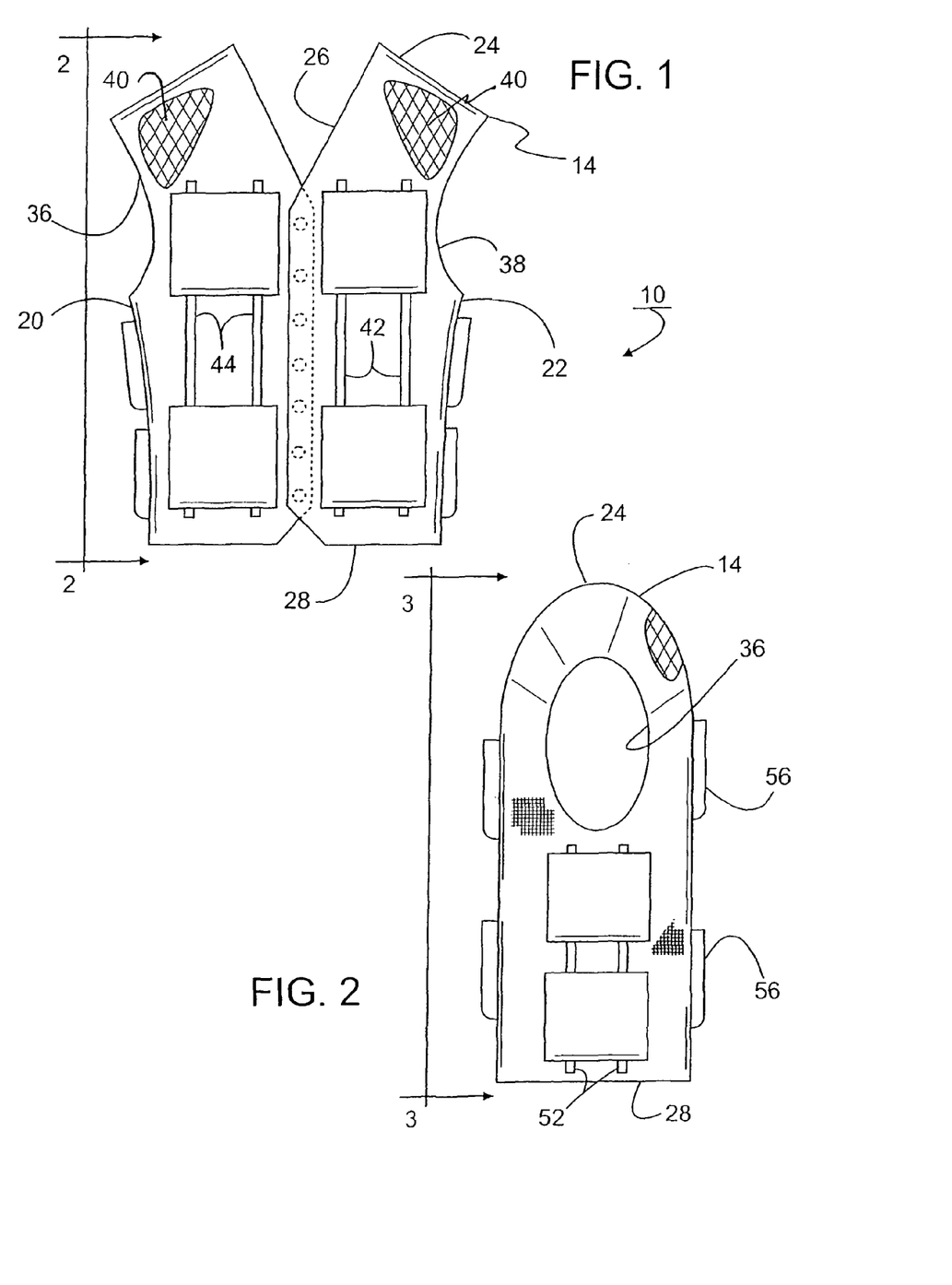
FIG. 1 is a front elevational view of a comfort enhancing vest system constructed in accordance with the principles of the present invention.
FIG. 2 is a side elevational view of the system taken along line 2-2 of FIG. 1.

With reference now to the drawings, and in particular to FIG. 1 thereof, the preferred embodiment of the new and improved comfort enhancing vest system embodying the principles and concepts of the present invention and generally designated by the reference numeral 10 will be described.

The present invention, the comfort enhancing vest system 10 is comprised of a plurality of components. Such components in their broadest context include a vest, a plurality of fixed coupling strips and a plurality of similarly configured envelopes. Such components are individually configured and correlated with respect to each other so as to attain the desired objective.

Figures 3, 4:
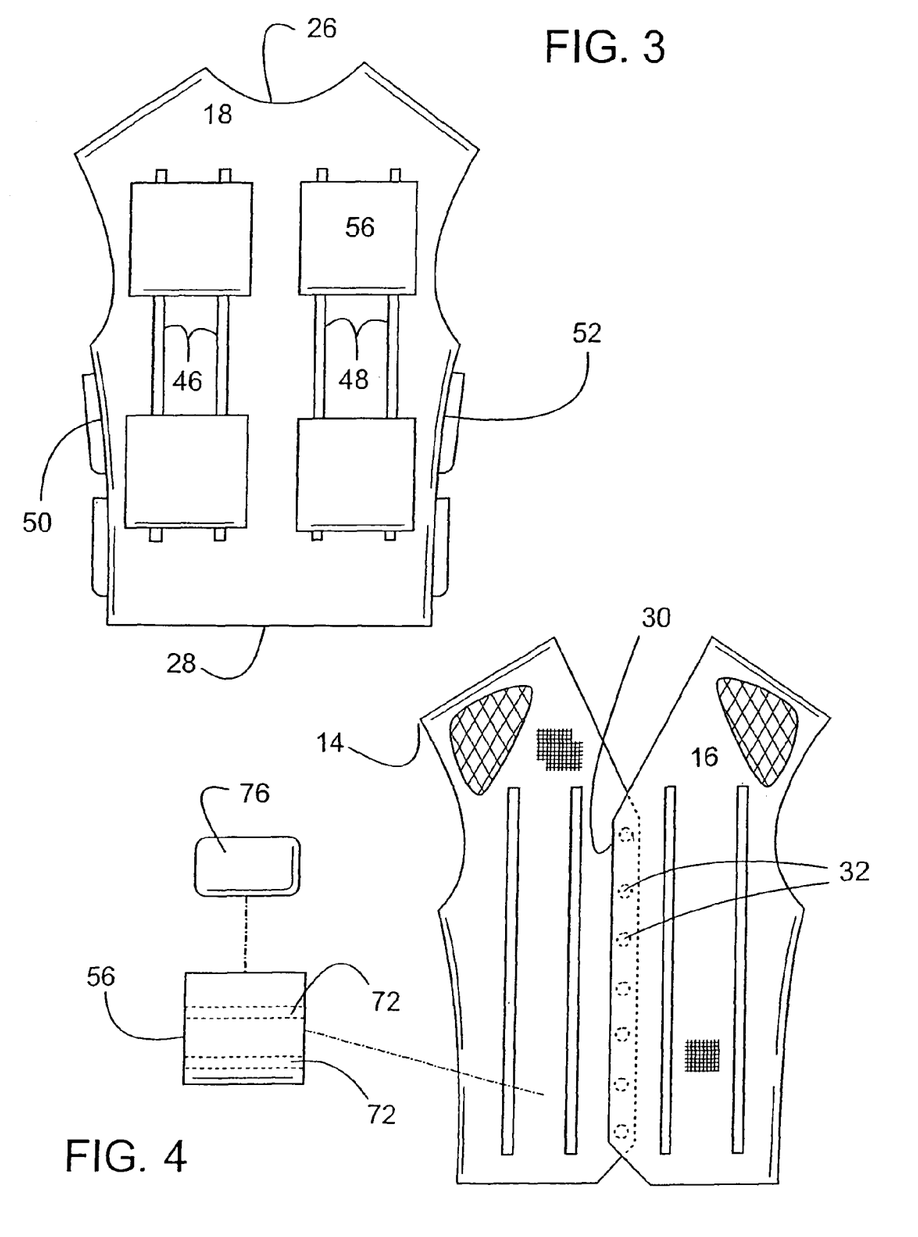
FIG. 3 is a rear elevational view of the system taken along line 3-3 of FIG. 2.
FIG. 4 is an exploded front elevational view of the comfort enhancing vest system shown in FIG. 1.

First provided is a vest 14. The vest has a front 16. The vest has a back 18. The vest has a left side 20. The vest has a right side 22. The sides are provided between the front and back. The vest also has a top 24. The top has a neck hole 26. The top has a bottom edge 28. The front has a centrally positioned, vertically oriented opening 30. The front has snaps 32. In this manner the opening is selectively joined during use. Further in this manner the opening is separated during putting on and taking off of the vest. The vest has a left arm hole 36. The left arm hole is provided in the left side beneath the top. The vest has a right arm hole 38. The right arm hole is provided in the right side beneath the top and spaced from the bottom edge. Optionally provided are recoil patches 40 in the upper front areas.

A plurality of exterior fixed coupling strips is provided next. The fixed coupling strips are secured to the vest in pairs. The strips of each pair are vertically oriented and spaced apart by between 3 inches and 4 inches. The fixed coupling strips include a long left front pair 42. The fixed coupling strips include a long right front pair 44. The fixed coupling strips include a long left back pair 46. The fixed coupling strips also include a right back pair 48. The long pairs are between 17 inches and 20 inches in length. The fixed coupling strips include a short left side pair 50. The short left side pair is provided between the left arm hole and the bottom edge. The fixed coupling strips include a short right side pair 52. The short right side pair is provided between the right arm hole and the bottom edge. The short pairs have a length of between 65 percent and 70 percent of the length of the long pairs. The strips of each pair are spaced from the next adjacent strip by between 3.5 inches and 4.5 inches.

Figure 5:
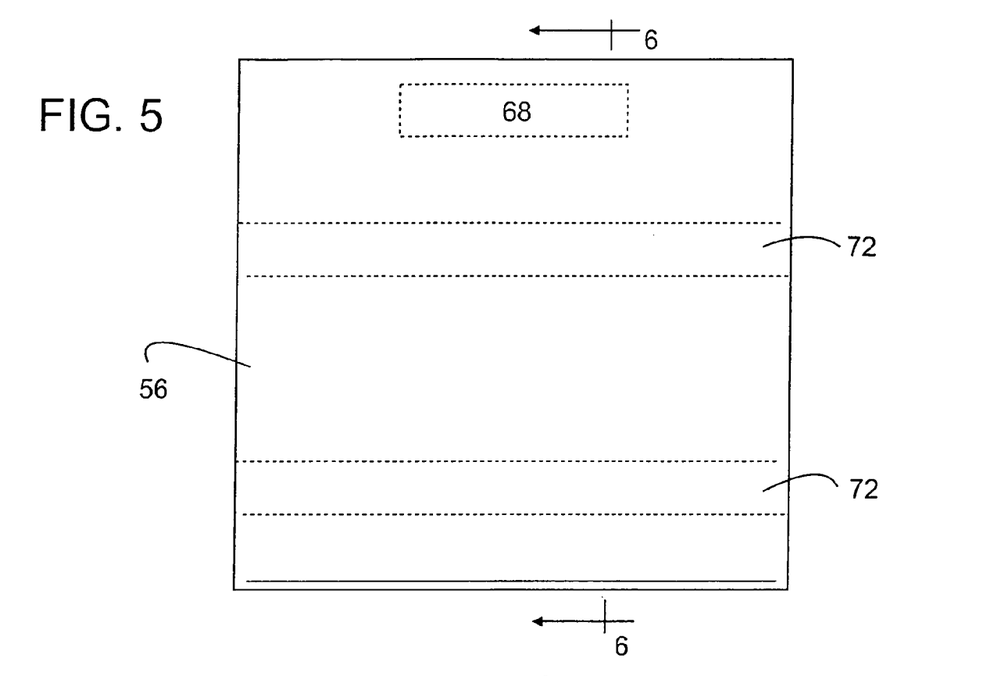
FIG. 5 is a front elevational view of one of the envelopes shown in the prior Figures.
Figure 6:
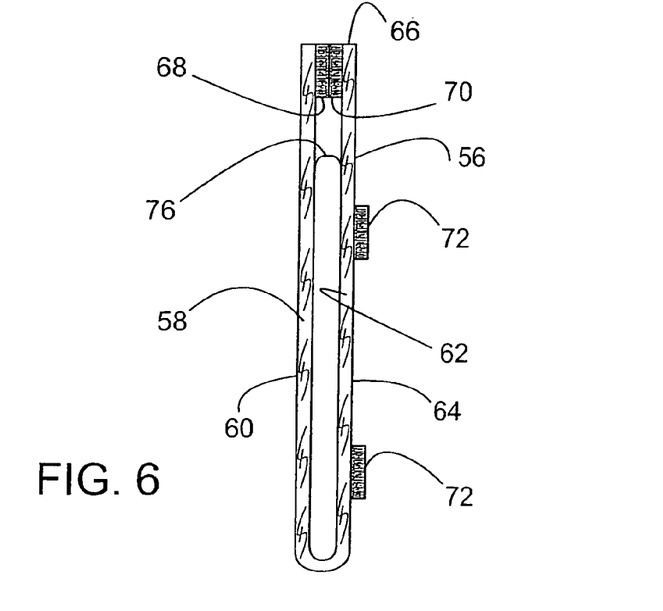
FIG. 6 is a cross sectional view taken along line 6-6 of FIG. 5.
Figure 7:
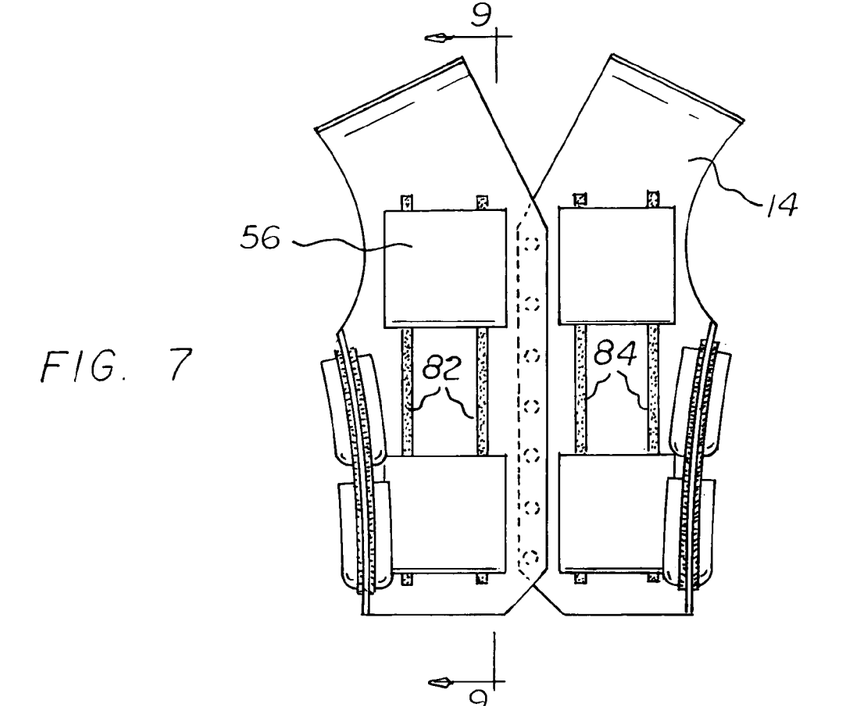
FIG. 7 is a front elevational view of the system illustrated inside out.
Figure 8:
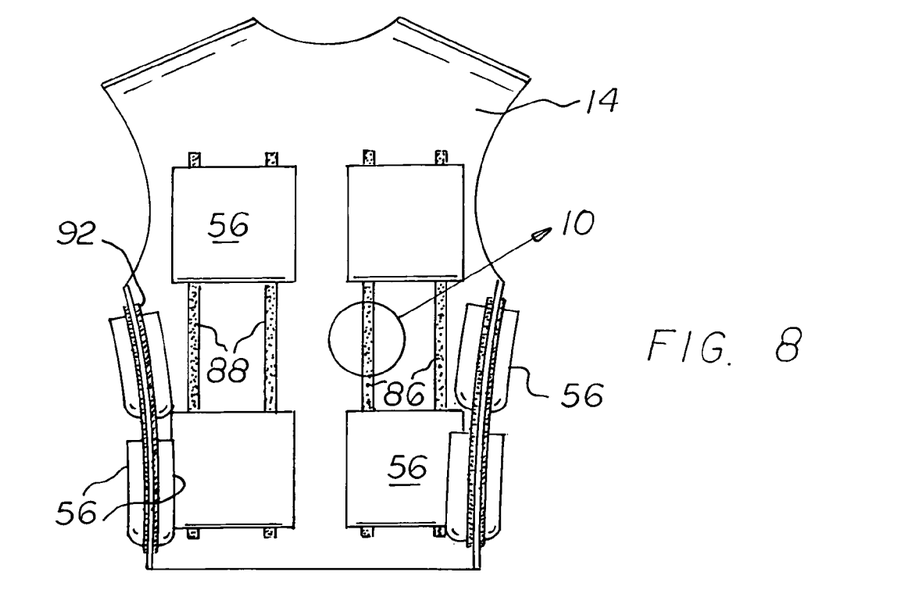
FIG. 8 is a rear elevational view of the system illustrated inside out.
Figure 9:
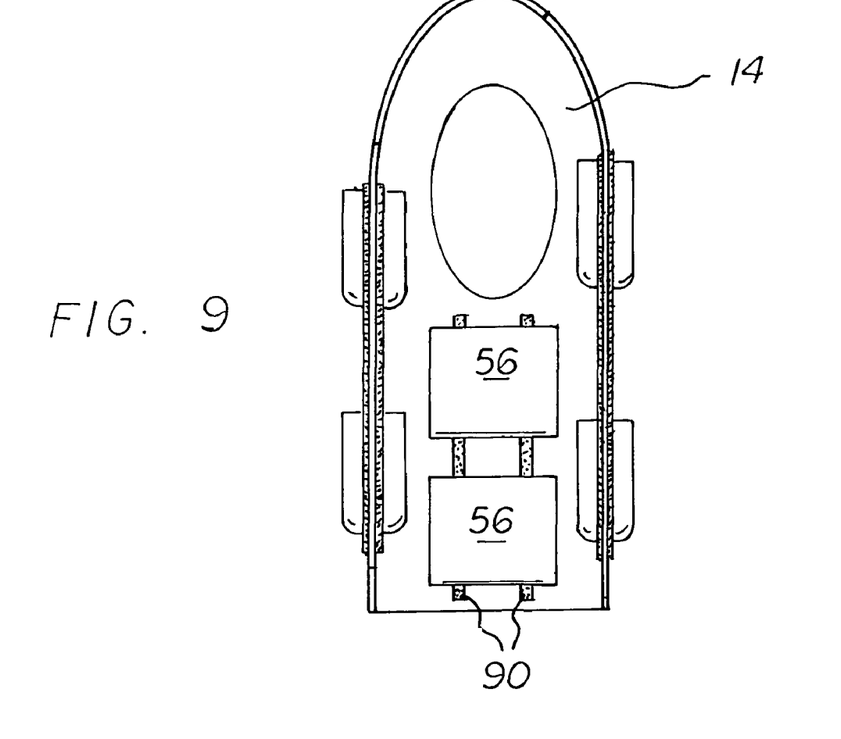
FIG. 9 is a cross sectional view taken along line 9-9 of FIG. 7.
Figure 10:
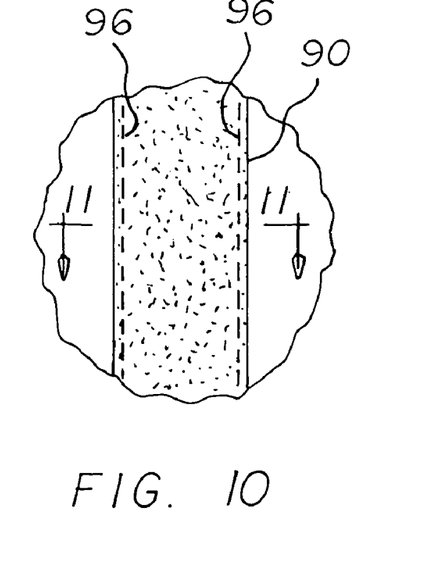
FIG. 10 is an enlarged illustration taken at circle 10 of FIG. 8.

Further provided is a plurality of similarly configured rectangular envelopes 56, each between 3 inches and 4 inches per side. Each envelope has a front panel 58. The front panel has a front face 60. Each envelope has a rear panel 62. The rear panel has a rear face 64. The panels are joined peripherally. Each envelope has an open upper edge 66. The upper edge is horizontally disposed. The upper edge has hook and loop closures 68, 70. In this manner the upper edge is opened and closed. Each envelope has a plurality of repositionable coupling strips 72. The repositionable coupling strips are secured to the rear faces of the envelopes in pairs. The repositionable coupling strips of each pair are horizontally oriented and spaced apart by between 3 inches and 4 inches. The repositionable coupling strips include one pair of strips 72 for each envelope.

Provided next is a heat generating thermal packet 76. The heat generating thermal packet is in a generally rectangular configuration between 2.5 and 3.5 inches on a side. The thermal packets are essentially flat for removable positioning within an envelope. Each thermal packet is filled with materials which when exposed to air or when the packet is rubbed or otherwise activated will generate heat. In this manner heat is generated for a predetermined period of time. Further in this manner an adjacent portion of a user's body is warmed. The thermal packets are filled, in the preferred embodiment, with various materials that when exposed to air will generate heat. Such various materials typically include iron powder, water, salt, activated charcoal and wood fibers. Consider for example, Hot Hands™ described at www.heatmax.com, the subject matter of which is incorporated herein by reference. In an alternate embodiment, thermal packets which generate heat when they are rubbed are provided. Two vertically spaced envelopes with thermal packets are positionable on each side. Two vertically spaced envelopes are positioned between a side and a front fixed coupling strip. Two vertically spaced envelopes are also positioned between a side and a rear fixed coupling strip. Three vertically spaced envelopes with thermal packets are positionable on each long pair of fixed coupling strips. Three vertically spaced envelopes are positioned between the front left and front right fixed coupling strips. Three vertically spaced envelopes are also positioned between the rear left and rear right fixed coupling strips.

In addition to the coupling strips on the exterior of the vest as described above, a plurality of coupling straps are provided in the interior of the vest. Note FIGS. 7 through 11. More specifically, as with the exterior strips, the interior fixed coupling strips are secured to the vest in pairs. The strips of each pair are vertically oriented and spaced apart by between 3 inches and 4 inches. The fixed coupling strips include a long left front pair 82. The fixed coupling strips include a long right front pair 84. The fixed coupling strips include a long left back pair 86. The fixed coupling strips also include a right back pair 88. The long pairs are between 17 inches and 20 inches in length. The fixed coupling strips include a short left side pair 90. The short left side pair is provided between the left arm hole and the bottom edge. The fixed coupling strips include a short right side pair 92. The short right side pair is provided between the right arm hole and the bottom edge. The short pairs have a length of between 65 percent and 70 percent of the length of the long pairs. The strips of each pair are spaced from the next adjacent strip by between 3.5 inches and 4.5 inches.

In the preferred embodiment, the vest 14 is fabricated of a woven cotton material for providing an essentially inextensible, non-sagging support surface for the pockets and the packets. The heat stays in intended locations. In addition, the natural material of the vest minimizes heat transfer through the vest. As such, the heat from the interior packets provide maximum heat with maximum efficiency. The heat from the exterior packets provide minimum heat if desired. The heat from the interior and exterior packets provide absolute maximum heat when desired.

Figure 11:
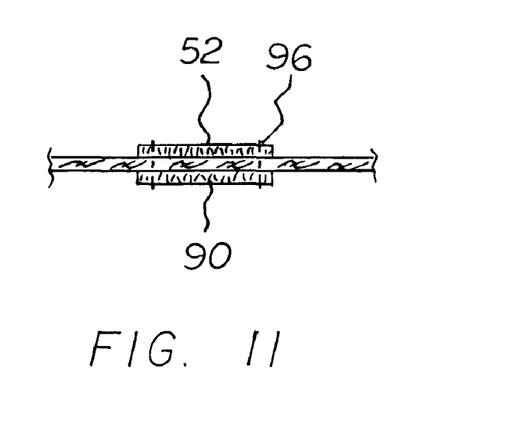
FIG. 11 is a cross sectional view taken along line 11-11 of FIG. 10.

Each coupling strip is coupled to the vest by peripheral lines of stitching 96. Each line of stitching extends through an exterior coupling strip and vest and interior coupling strip. In addition to using the stitching efficiently, the alignment of the exterior and interior coupling strips insures that the exterior and interior packets, overlie one another for maximizing the efficiency of the heat from the packets.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accord-

What is claimed as being new and desired to be protected by Letters Patent of the United States is as follows:

1. A comfort enhancing vest system for enabling selective application of warmth to various portions of a wear's body, comprising:

a vest having an interior and exterior formed with a front and a back with a left and a right side between the front and the back, the vest having a top with a neck hole and a bottom edge, the front having a centrally positioned, vertically orientated opening with snaps for selectively joining the opening during use and separating the opening during putting on and taking off of the vest, a left arm hole in the left side beneath the top and spaced from the bottom edge and a right arm hole in the right side beneath the top and spaced from the bottom edge, the vest being fabricated of a woven cotton material for providing a support surface, wherein the woven cotton material of the vest minimizes heat transfer through the vest;

a plurality of exterior fixed coupling strips secured to the exterior of the vest in pairs, the strips of each pair being vertically orientated and spaced apart by between 3 inches and 4 inches, the plurality of exterior fixed coupling strips including a long left front pair and a long left right pair and a long left back pair and a long right back pair, the long pairs being between 17 inches and 20 inches in length, the plurality of exterior fixed coupling strips further include a short left side pair between the left arm hole and the bottom edge and a short right side pair between the right arm hole and the bottom edge, the short pairs having a length of between 65 percent and 70 percent of the length of the long pairs, the strips of each pair being spaced from the next adjacent pair by between 3.5 inches and 4 inches;

a plurality of interior fixed coupling strips secured to the interior of the vest in pairs, the plurality of interior fixed coupling strips including a long left front pair and a long left right pair and a long left back pair and a long right back pair, the long pairs being between 17 inches and 20 inches in length, the plurality of interior coupling strips further including a short left side pair between the left arm hole and the bottom edge and a short right side pair between the right arm hole and the bottom edge, the short pairs having a length of between 65 percent and 70 percent of the length of the long pairs, the strips of each pair being spaced from the next adjacent pair by between 3.5 inches and 4 inches;

lines of stitching extending through the plurality of exterior coupling strips and the vest and the plurality of interior coupling strips to ensure that the exterior and interior plurality of coupling strips overlie one another;

a plurality of rectangular envelopes, each between 3 inches and 4 inches per side, each envelope having a front panel with a front face and a rear panel with a rear face, the panels being joined peripherally with an upper edge including an opening, the upper edge being horizontally disposed, the upper edge including hook and loop closures for opening and closing the opening, a plurality of coupling strips secured to the rear face of the envelopes in pairs, the strips of each pair being horizontally orientated and spaced apart by 3 inches to 4 inches, the plurality of coupling strips including one pair of strips for each envelope and a heat generating packet in a generally rectangular configuration between 2.5 and 3.5 inches on a side, the thermal packet being essentially flat for removable positioning within the plurality of rectangular envelopes, each thermal packet being filled with materials adapted to generate heat to warm an adjacent portion;

wherein two vertically spaced rectangular envelopes with thermal packets are positionable on the short left side pair and the short right side pair of the exterior and interior plurality of fixed coupling strips and three vertically spaced rectangular envelopes with thermal packets are positionable on the long left front pair and the long right front pair of the exterior and interior plurality of fixed coupling strips such that the rectangular envelopes with thermal packets positioned on the exterior and interior plurality of fixed coupling strips overlie one another.

* * * * *